United States Patent
Hobot et al.

(10) Patent No.: US 7,065,394 B2
(45) Date of Patent: Jun. 20, 2006

(54) GUIDE CATHETER

(75) Inventors: Christopher M. Hobot, Tonka Bay, MN (US); Stanten C. Spear, Arden Hills, MN (US); James F. Kelley, Coon Rapids, MN (US); Jennifer L. Braunschweig, Minneaplois, MN (US); Kiem Dang, Minneapolis, MN (US); Kenneth C. Gardeski, Plymouth, MN (US)

(73) Assignee: Medtronic, Inc, Minneapolis, MN (US)

( * ) Notice: Subject to any disclaimer, the term of this patent is extended or adjusted under 35 U.S.C. 154(b) by 525 days.

(21) Appl. No.: 10/016,114

(22) Filed: Dec. 12, 2001

(65) Prior Publication Data

US 2003/0109823 A1 Jun. 12, 2003

(51) Int. Cl.
*A61B 5/05* (2006.01)

(52) U.S. Cl. ................................. 600/424; 606/108
(58) Field of Classification Search ............... 623/1.11; 604/103.09, 103.1; 600/462–463, 458–459, 600/585–586, 424
See application file for complete search history.

(56) References Cited

U.S. PATENT DOCUMENTS

| | | | |
|---|---|---|---|
| 4,657,024 A | 4/1987 | Coneys | |
| 4,778,455 A * | 10/1988 | Kousai et al. | 604/270 |
| 4,955,862 A | 9/1990 | Sepetka | |
| 5,081,997 A * | 1/1992 | Bosley et al. | 600/458 |
| 5,201,314 A | 4/1993 | Bosley et al. | |
| 5,255,690 A | 10/1993 | Keith et al. | |
| 5,300,048 A | 4/1994 | Drewes, Jr. et al. | |
| 5,324,269 A | 6/1994 | Miraki | |
| 5,403,292 A * | 4/1995 | Ju | 604/527 |
| 5,584,821 A | 12/1996 | Hobbs et al. | |
| 5,908,413 A | 6/1999 | Lange et al. | |
| 5,921,933 A * | 7/1999 | Sarkis et al. | 600/459 |
| 5,967,988 A | 10/1999 | Briscoe et al. | |
| 6,106,473 A | 8/2000 | Violante et al. | |
| 6,143,013 A | 11/2000 | Samson et al. | |
| 6,171,295 B1* | 1/2001 | Garabedian et al. | 604/524 |
| 6,641,776 B1* | 11/2003 | Weaver et al. | 264/642 |
| 6,905,458 B1* | 6/2005 | Choay et al. | 600/34 |
| 2001/0037065 A1* | 11/2001 | Graf et al. | 600/452 |

FOREIGN PATENT DOCUMENTS

| | | |
|---|---|---|
| EP | 0 666 086 A1 | 8/1995 |
| EP | 0 714 673 A2 | 6/1996 |
| EP | 1 062 965 A1 | 12/2000 |
| FR | 2 571 621 | 4/1986 |

* cited by examiner

*Primary Examiner*—(Jackie) Tan-Uyen T. Ho
(74) *Attorney, Agent, or Firm*—Michael C. Soldner; Girma Wolde-Michael

(57) ABSTRACT

A guide catheter has properties that promote enhanced visibility of the guide catheter using fluoroscopic or ultrasonic imaging techniques. The tip of the guide catheter may incorporate a material that is both fluoro and echo visible. The first material also may be provided in various amounts along the length of the guide catheter. In addition, the guide catheter may incorporate a reinforcing braid that includes one or more strands of a second material that is radio-opaque. As a result, the result guide catheter achieves improved radio-opacity and echogenicity.

11 Claims, 4 Drawing Sheets

GUIDE CATHETER

The invention relates generally to catheters and, more particularly, to guide catheters for introducing catheters, electrode leads and the like into the body of a patient.

BACKGROUND

Guide catheters are used to place catheters, electrode leads and the like in desired locations within the body of a patient. A guide catheter typically includes an elongated sheath that is inserted into a blood vessel or another portion of the body. A catheter or lead is introduced through an inner channel defined by the sheath.

When the catheter or lead is intended to remain in the body for an extended period of time, the sheath is typically removed. To ease removal, some guide catheters are constructed to permit longitudinal slitting. Specifically, the proximal end of the catheter may be fitted with a slitting instrument that serves to slit the sheath along its length. The slitting instrument facilitates removal of the sheath from the body of the patient, leaving the catheter or lead in place.

To enable precise positioning of a catheter or lead, the guide catheter often comprises fluoro or echo visible materials. Using fluoroscopic or ultrasonic imaging techniques, the physician can visualize the guide catheter, and place the catheter or electrode lead in a desired position. Guide catheters typically incorporate radio-opaque or echogenic materials to promote visibility. Unfortunately, some of the materials can make slitting the guide catheter for removal more difficult.

SUMMARY

The invention is directed to a slittable guide catheter with properties that promote enhanced visibility of the guide catheter using fluoroscopic or ultrasonic imaging techniques. The tip of the guide catheter may incorporate a material that is both fluoro and echo visible. The first material also may be provided along the length of the guide catheter. In addition, the guide catheter may incorporate a reinforcing braid that includes one or more strands of a second material that is radio-opaque. As a result, the guide catheter may achieve improved radio-opacity and echogenicity.

The first material may take the form of jet-milled tungsten carbide that is incorporated in polymeric segments forming an outer sheath of the guide catheter. The tungsten carbide may be added to the polymeric material in the amount of approximately 40 to 75 percent by weight. The jet milled tungsten carbide material offers exceptional echogenicity and, when added to the polymeric material, permits ready slitting along the length of the guide catheter.

The second material may take the form of platinum iridium, gold, tantalum, platinum, tungsten carbide, and other radio-opaque materials. The second material is formed into strands that are braided among steel strands forming a reinforcing braid for the guide catheter. Incorporation of a relatively small number of strands, e.g., one to three strands, can significantly improve fluoro visibility of the guide catheter.

In one embodiment, the invention provides a guide catheter comprising an elongated sheath having proximal end, a distal tip, and an inner lumen sized to accommodate travel of medical components. The guide catheter further includes a first material in the distal tip, wherein the first material is radio-opaque and echogenic, and a second material in a wall of the sheath, wherein the second material is radio-opaque.

In another embodiment, the invention provides a guide catheter comprising an elongated sheath having proximal end, a distal tip, and an inner lumen sized to accommodate travel of medical components, and a first material in the distal tip, wherein the first material is radio-opaque and echogenic, and includes tungsten carbide particles having an average diameter of less than 500 nanometers.

In an added embodiment, the invention provides a guide catheter comprising an elongated sheath having proximal end, a distal tip, and an inner lumen sized to accommodate travel of medical components, and a reinforcing braid formed in a wall of the sheath, wherein at least one of strand in the reinforcing braid is formed from a radio-opaque material.

The invention can provide a number of advantages. In particular, the invention is capable of promoting enhanced visibility of a guide catheter using both fluoroscopic and ultrasonic imaging techniques. This feature provides a physician with flexible imaging options. The guide catheter can be used by physicians who prefer fluoroscopic imaging, for example, as well as those who prefer ultrasound. In each case, the physician may select the same guide catheter without regard to the desired imaging modality.

The use of a single material as an additive to enable both fluoroscopic and ultrasonic imaging allows the overall additive level to be lower, which tends to preserve the mechanical properties of the composite blend and the slittability of the guide catheter. In this manner, the first material can be loaded into the polymeric sheath material in amounts that promote visibility but maintain slittability. Also, the second material can be integrated with a conventional reinforcing braid without adversely affecting slitting. These advantages are generally in contrast to radio-opaque bands and other features that can make the guide catheter difficult to slit for removal.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
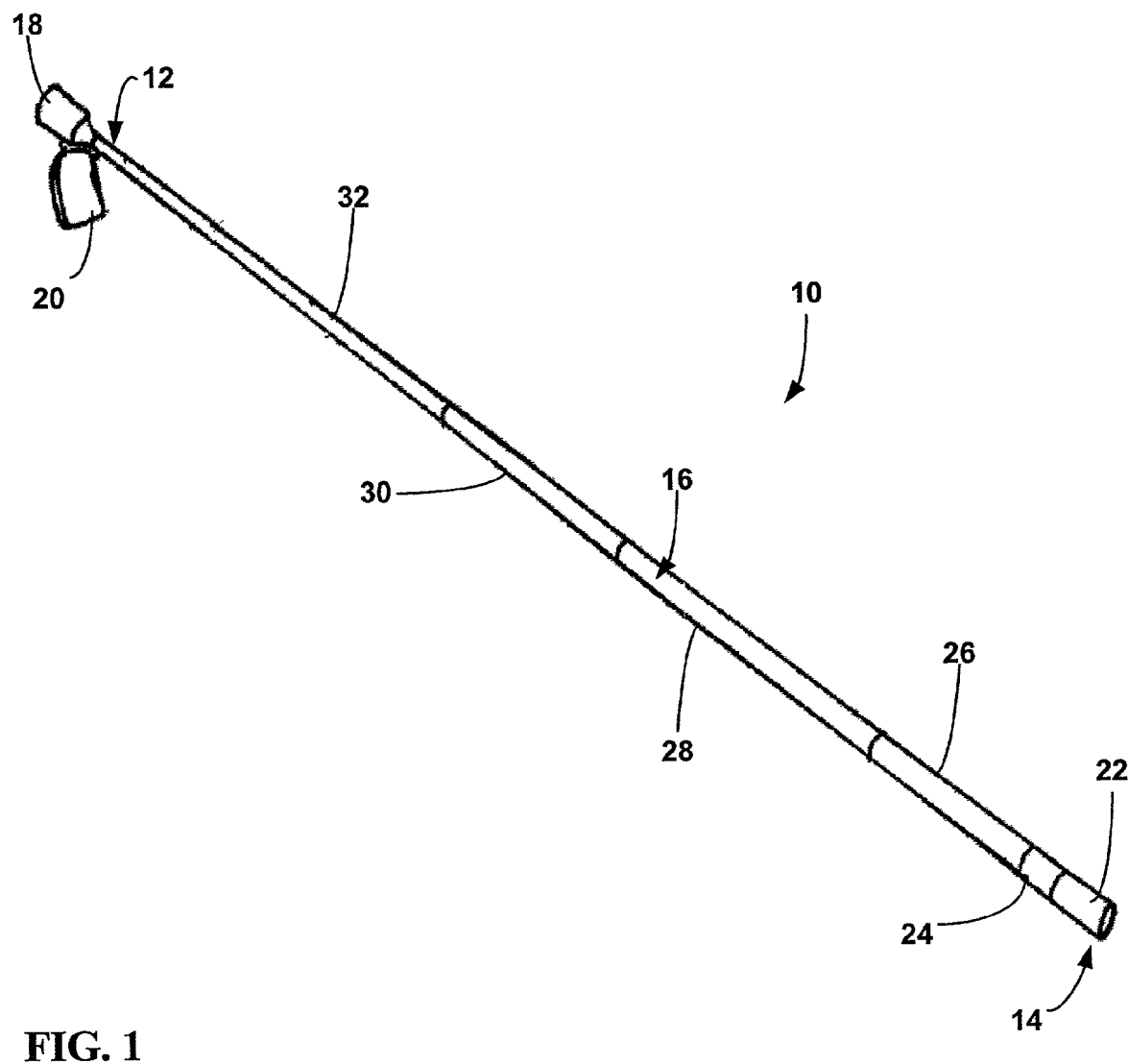
FIG. 1 is a perspective view of a guide catheter.

FIG. 1 is a perspective view of a guide catheter 10. As shown in FIG. 1, guide catheter 10 includes a proximal end 12, distal tip 14, and an elongated sheath 16 extending between the proximal and distal ends. Guide catheter 10 is sized for insertion into a lumen, such as a blood vessel, within the human body. Guide catheter 10 defines an inner channel (not shown in FIG. 1) through which other elements such as catheters and electrode leads may be inserted. A luer fitting 18 and handle 20 may be coupled to proximal end 12 of catheter 10. A slitter (not shown) may be positioned near proximal end 12, e.g., adjacent handle 20.

Figure 2:
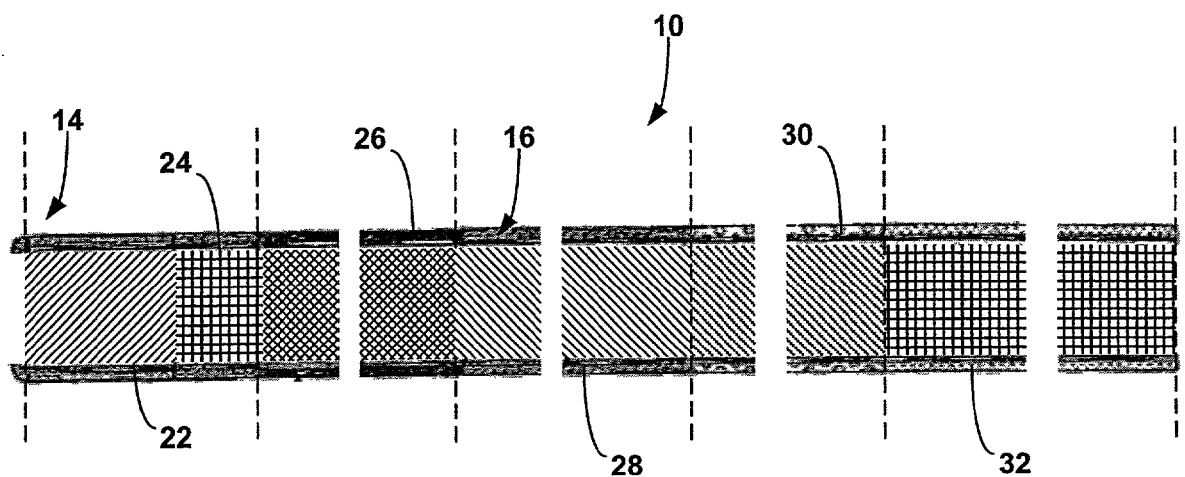
FIG. 2 is a cross-sectional side view of the guide catheter of FIG. 1 illustrating incorporation of a radio-opaque and echogenic material in the distal tip.

FIG. 2 is a cross-sectional side view of the guide catheter of FIG. 1 illustrating incorporation of a radio-opaque and echogenic material in the distal tip of guide catheter 10. As shown in FIGS. 1 and 2, sheath 16 may include a number of sheath segments 22, 24, 26, 28, 30, 32 disposed along the length of catheter 10. Sheath 16 may be formed to provide either a straight or pre-bent shape to guide catheter 10, depending on the desired end application.

Sheath 16 is made from a material that permits slitting along the length of catheter 10 and promotes maneuverability. In particular, each sheath segment 22, 24, 26, 28, 30, 32 may be constructed of a polymeric material, such as polyether block amide, nylon block polymer, silicone, or polyurethane, as well as composites or mono-polymers. An example of one suitable polymeric material is the polyether block amide marketed under the trademark PEBAX® and commercially available from Atofina Chemicals Inc., of King of Prussia, Pa.

Guide catheter 10 is constructed to exhibit properties that promote enhance visibility of the using fluoroscopic or ultrasonic imaging techniques. With reference to FIG. 1, sheath segment 22 forms a distal tip of guide catheter 10, and incorporates a material that is both fluoro and echo visible. The material also may be provided along the length of the guide catheter. For example, the material may be distributed continuously along the length of catheter 10 or at intermittent positions.

The material incorporated in distal tip 22 is tungsten carbide, which exhibits both radio-opacity and echogenicity. For enhanced echogenicity, the tungsten carbide may be jet milled and have an average particle size of less than approximately 500 nanometers and, more preferably, less than approximately 200 nanometers. The particle size may refer generally to a diameter of width of the tungsten carbide particles, although spherical particles are not necessary. Particle sizes in the above ranges may provide increased surface area for reflection of ultrasonic energy, thereby enhancing visibility of portions of guide catheter 10 in which the particles are dispersed. At the same time, tungsten carbide is highly radio-opaque, and facilitates fluoroscopic imaging of guide catheter 10.

The same tungsten carbide particles can be incorporated along the length of guide catheter 10 in sheath segments 24, 26, 28, 30, 32. In particular, the tungsten carbide particles can be dispersed in polymeric material that is molded or extruded to form sheath 16. Alternatively, in one embodiment, the tungsten carbide may be provided in sheath segment 22 in distal tip 14 and sheath segment 24, with the remaining sheath segments 26, 28, 30, 32 carrying barium sulfate particles.

Each sheath segment 22, 24, 26, 28, 30, 32 may be constructed from a similar material with a similar concentration of tungsten carbide particles. However, sheath segments 22, 24, 26, 28, 30, 32 may have different hardness characteristics. As a particular illustration, sheath segments 22, 24, 26, 28, 30, 32 may be constructed from PEBAX material with 25, 35, 55, 63 and 72 Shore D hardnesses, respectively. The tungsten carbide particles can be added to sheath segments 22, 24, 26, 28, 30, 32 in a concentration on the order of approximately 40 to 75 percent by weight without significantly degrading the overall mechanical properties of guide catheter 10.

As one particular example, the tungsten carbide may be added to the polymeric material in the amount of approximately 70 to 75 percent by weight and, more preferably, approximately 73 to 74 percent by weight. In an exemplary embodiment, the jet milled tungsten carbide material is added to the polymeric material in a weight of approximately 73.2 percent by weight. A concentration of 73.2 percent by weight (tungsten carbide particles to PEBAX™ Shore D material corresponds to a concentration of approximately 15 percent by volume. The barium sulfate particles may be added to sheath segments 26, 28, 30, 32 in the amount of approximately 25 to 35 percent by weight and, more preferably, approximately 30 percent by weight.

The jet milled tungsten carbide particles offer exceptional echogenicity and, when added to the polymeric material, permit ready slitting along the length of guide catheter 10. For these reason, in determining the concentration of tungsten carbide particles, it is desirable to balance the degree of echogenicity against the slittability of sheath 16. As more tungsten carbide particles are added to segments 22, 24, 26, 28, 30, 32, the material forming guide catheter 10 becomes difficult to process and, in some cases, difficult to maneuver for insertion into and removal from the body of a patient. A guide catheter 10 constructed as described herein retains desirable mechanical properties, enabling ease of maneuverability and atraumatic use.

Figure 3:
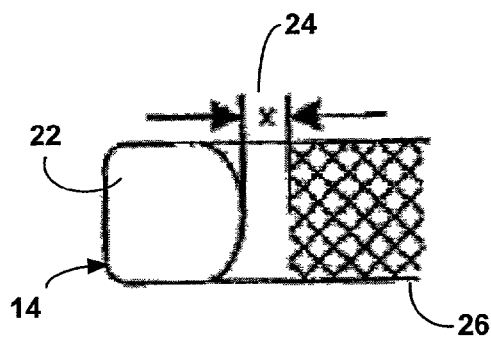
FIG. 3 is an enlarged cross-sectional side view of the distal tip of the guide catheter shown in FIGS. 1 and 2.

FIG. 3 is an enlarged cross-sectional side view of distal tip 14 of guide catheter 10. As shown in FIG. 3, distal tip 14 may comprise a sheath segment 22 that is separated from sheath segment 26 by in intermediate sheath segment 24. Sheath segment 24 may provide a spacing "x" between sheath segments 22, 26. In particular, a reinforcing braid (not shown in FIG. 3) may extend along substantially the entire length of guide catheter 10 and be embedded between inner and outer walls of sheath 16. However, the distal end of the reinforcing braid terminates in sheath segment 26, and does not extend into distal tip 14. The distance "x" may be on the order of 0.25 to 0.35 inches (0.64 to 0.89 centimeters).

Figure 4:
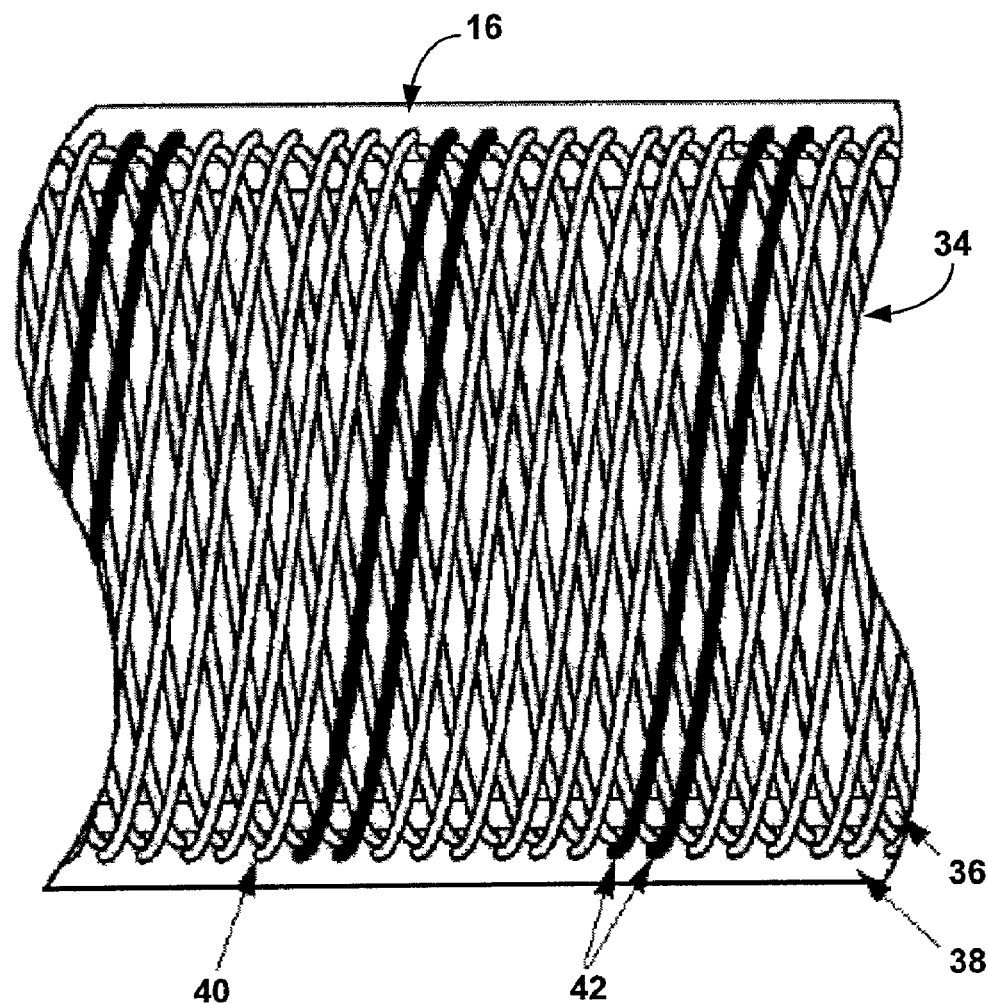
FIG. 4 is a side view of the guide catheter of FIG. 1 with an exposed illustration of a reinforcing braid with radio-opaque strands.

FIG. 4 is a side view of guide catheter 10 with an exposed illustration of a reinforcing braid 34. Reinforcing braid 34 is substantially tubular in shape, and includes an inter-woven array of strands 40. Braid 34 may be formed between inner wall 36 and outer wall 38 of sheath 16. To promote visibility, some of the strands may be radio-opaque. In particular, in the example of FIG. 4, two strands 42 are formed from a radio-opaque material. The radio-opaque material use in strands 42 may be formed from a variety of materials such as platinum iridium, gold, tantalum, platinum, tungsten carbide, and the like. Strands 42 may be formed from a variety of conventional materials such as steel. Thus, the radio-opaque material is formed into strands that are braided among the steel strands. Incorporation of a relatively small number of strands, e.g., one to three strands, can significantly improve fluoro visibility of the guide catheter.

Figure 5:
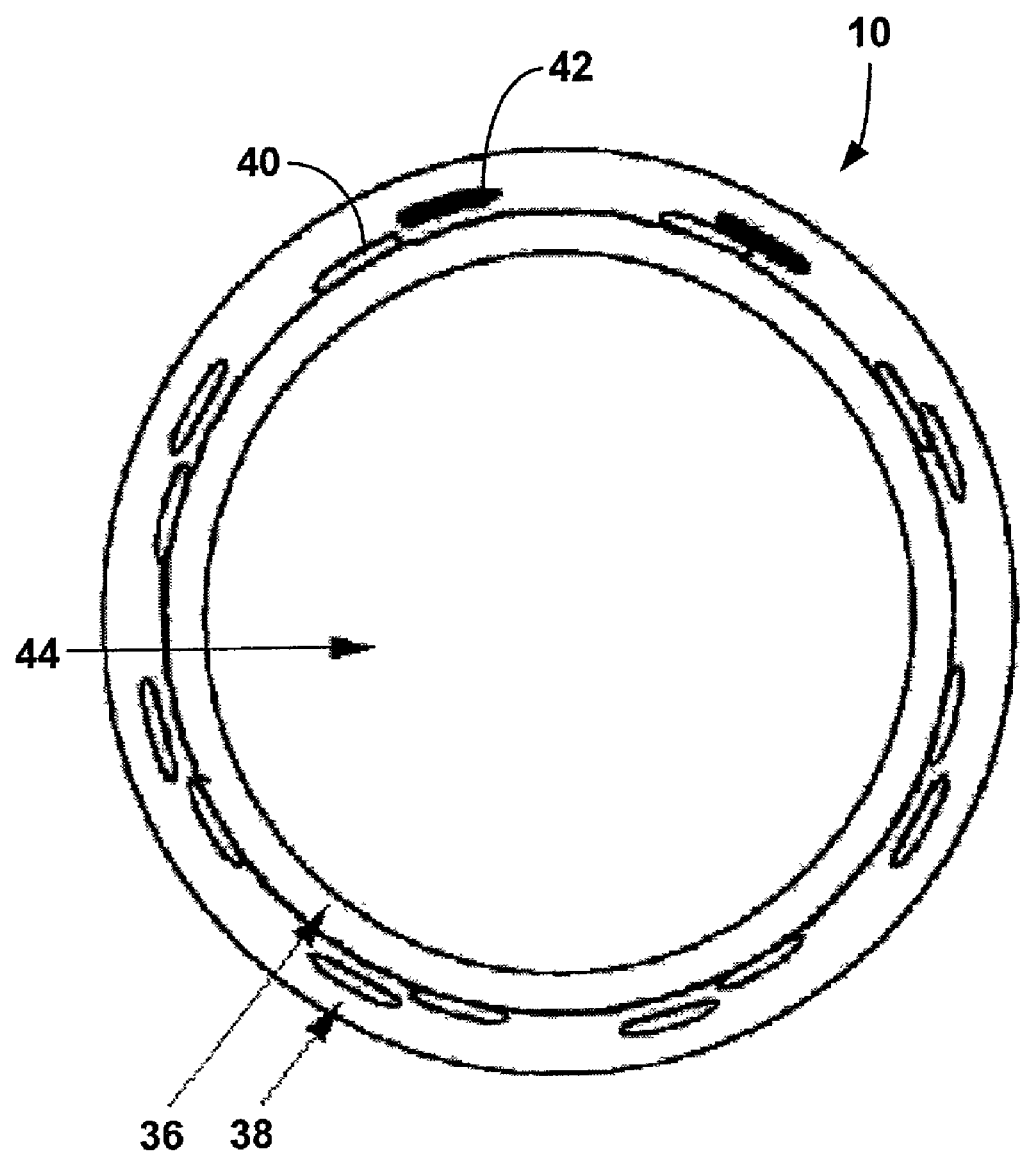
FIG. 5 is a cross-sectional view of the inner lumen and sheath of the guide catheter of FIG. 1.

FIG. 5 is a cross-sectional view of the inner channel 44 and sheath 16 of guide catheter 10. Incorporation of strands 42 promotes visibility but does not significantly affect the mechanical properties of guide catheter 10. With strands 42, guide catheter 10 remains readily slittable, unlike other types of guide catheters that may use radio-opaque marker bands. In addition, use of radio-opaque strands 42 offsets the need to provide additional radio-opaque material within walls 36, 38. This is advantageous because loading excessive amounts of radio-opaque material into walls 36, 38 can also make the material forming sheath 16 difficult to process.

Various embodiments of the invention have been described. These and other embodiments are within the scope of the following claims.

The invention claimed is:

1. A guide catheter comprising:
an elongated sheath having proximal end, a distal tip, and an inner channel to accommodate travel of a medical component;
a first material in the distal tip, wherein the first material is radio-opaque and echogenic; and
a second material in a wall of the sheath, wherein the second material is a reinforcing braid formed within the sheath, wherein the braid includes a plurality of strands and at least one strand of the plurality of strands forming the reinforcing braid includes a radio-opaque material, and wherein jet-milled tungsten carbide particles are distributed within the polymeric material of the first material between approximately 70 to 75 percent by weight and have an average diameter approximately less than or equal to 500 nanometers.

2. The guide catheter of claim 1, wherein the sheath includes a plurality of sheath segments extending along the length of the guide catheter, and each of the plurality of sheath segments is formed of a polymeric material containing jet-milled tungsten carbide particles.

3. The guide catheter of claim 1, wherein the radio-opaque material comprises a material selected from the group consisting of platinum iridium, gold, tantalum, platinum, and tungsten carbide.

4. A guide catheter comprising:
an elongated sheath having proximal end, a distal tip, and an inner lumen sized to accommodate travel of medical components; and
a first material in the distal tip, wherein the first material is radio-opaque and echogenic, and includes jet-milled tungsten carbide particles having an average diameter of less than 500 nanometers, and wherein the tungsten carbide articles are distributed within the polymeric material in the amount of approximately 70 to 75 percent by weight.

5. The guide catheter of claim 4, wherein the distal tip is formed of a polymeric material, and the first material comprises jet-milled tungsten carbide particles distributed within the polymeric material.

6. The guide catheter of claim 5, wherein the sheath includes a number of sheath segments extending along the length of the guide catheter, and each of the sheath segments is formed of a polymeric material containing jet-milled tungsten carbide particles.

7. The guide catheter of claim 6, wherein the polymeric material comprises a polyether block amide.

8. A guide catheter comprising:
an elongated sheath having proximal end and a distal tip;
a first material forming the distal tip, wherein the first material is formed of a polymeric material and jet-milled tungsten carbide particles; and
a second material forming a wall of the sheath, wherein the second material is formed of a polymeric material and jet-milled tungsten carbide particles are distribute within a first portion of the polymeric material of the second material in an amount between approximately 40 to 75 percent by weight, wherein the jet-milled tungsten carbide particles are distributed within the polymeric material of the first material between approximately 70 to 75 percent by weight and have an average diameter approximately less than or equal to 500 nanometers.

9. The guide catheter of claim 8, wherein the second material includes barium sulfate particles distributed within a second portion of the polymeric material of the second material different from the first portion.

10. The guide catheter of claim 8, wherein the jet-milled tungsten carbide particles have an average diameter approximately less than or equal to 500 nanometers.

11. A guide catheter comprising:
an elongated sheath having proximal end and a distal tip;
a first material forming the distal tip, wherein the first material is formed of a polymeric material and jet-milled tungsten carbide particles; and
a second material forming a wall of the sheath, wherein the second material is formed of a polymeric material and barium sulfate particles, and wherein the jet-milled tungsten carbide particles are distributed within the polymeric material of the first material between approximately 70 to 75 percent by weight and have an average diameter approximately less than or equal to 500 nanometers.

* * * * *